United States Patent [19]

Raether

[11] Patent Number: 4,861,758

[45] Date of Patent: Aug. 29, 1989

[54] COCCIDIOCIDAL COMPOSITIONS

[75] Inventor: Wolfgang Raether, Dreieich, Fed. Rep. of Germany

[73] Assignee: Hoechst Aktiengesellschaft, Frankfurt Am Main, Fed. Rep. of Germany

[21] Appl. No.: 118,321

[22] Filed: Nov. 9, 1987

[30] Foreign Application Priority Data

Nov. 11, 1986 [DE] Fed. Rep. of Germany ....... 3638445

[51] Int. Cl.$^4$ .................... A61K 31/44; A61K 31/47; A61K 31/70; A61K 31/505
[52] U.S. Cl. ........................................ 514/27; 514/25; 514/256; 514/259; 514/312; 514/345; 514/537
[58] Field of Search ................... 514/25, 27, 345, 312, 514/256, 259, 537

[56] References Cited

U.S. PATENT DOCUMENTS 4,278,663 7/1981 Liu et al. ................................ 514/27
4,340,596 7/1982 Schein .................................. 544/278

OTHER PUBLICATIONS

The Merck Index, 10th Ed. (1983), pp. 86, 144, 341, 544, 662, 928.

Primary Examiner—Allen J. Robinson
Attorney, Agent, or Firm—Finnegan, Henderson, Farabow, Garrett & Dunner

[57] ABSTRACT

Coccidiocidal compositions which contain the polyether antibiotic maduramicin or its salt in combination with one or more active substances from the group comprising meticlorpindol methyl benzoquate, amprolium, beclotiamine or halofuginone or its salts show synergistic effects.

12 Claims, No Drawings

COCCIDIOCIDAL COMPOSITIONS

Maduramicin is known as a polyether antibiotic from U.S. Pat. No. 4,278,663. There its use as an anticoccidiosis agent is also described. The compound is prepared by fermentation.

It has now been found that the action of maduramicin is increased beyond the expected extent when the latter is combined with other known coccidiocidal active substances.

The subject of the invention is therefore formed by coccidiocidal agents which contain maduramicin or its physiologically acceptable salt in combination with one or more active substances of the group comprising meticlorpindol, methyl benzoquate, amprolium, beclotiamine or halofuginone or its salt.

In particular, two-component combinations are suitable. According to the invention, three-component combinations can also be used; of the latter, the combination of maduramicin with meticlorpindol and methyl benzoquate.

The combination partners to be used according to the invention for maduramicin have been known for a fairly long time in veterinary medicine. They are all described in the Merck Index, 10th edition, published by Merck & Co., Inc. USA (1983): meticlorpindol (3,5-dichloro-2,6-dimethyl-4-pyridinol) on page 341; methyl benzoquate (nequinate; 3-methoxycarbonyl-6-n-butyl-7-benzyloxy-4-oxoquinoline on page 928; ethopabate (methyl 4-acetamido-2-ethoxybenzoate) on page 544; amprolium (1-[(4-amino-2-propyl-5-pyrimidinyl)methyl]-2-methyl-piperidinium chloride) on page 613; beclotiamine (3-[(4-amino-2-methyl-5-pyrimidinyl)methyl]-5-(2-chloroethyl)-4-methylthiazolium chloride) on page 144, and halofuginone (7-bromo-6-chlorofebrifugine) on page 662. In addition to halofuginone, their physiologically acceptable salts such as the hydrohalides, in particular hydrobromide, acetate, lactate, alkali or alkaline earth salt, aceturic acid (see German Offenlegungsschrift 2,934,069) are also covered according to the invention, and also all the optical isomers or their mixtures. Amprolium or beclotiamine may be employed in the form of their hydrochloride addition salts. Instead of beclotiamine, its corresponding naphthalene-1,5-disulfonic acid salt may be employed.

The combination of meticlorpindol and methyl benzoquate is known as the commercial product (R)Lerbek (manufactured by ICI). The combination of amprolium with ethopabate is on the market as the commercial product (R)Amprol Mix Super (Merck, Sharp & Dohme).

Maduramicin may be employed as free acid or as salt, in particular as ammonium salt or as alkali (Na, K) salt. Preferably the ammonium salt is used. The product is isolated and is employed in purified form after fermentation.

The combinations according to the invention exhibit synergistic effects in combating coccidiosis, in particular coccidiosis in poultry.

In the intensive husbandry of poultry in a confined space, for example broiler production or poultry rearing, there is always the potential risk of a coccidia infection, which, if not combated chemotherapeutically, leads to serious business losses, due to Eimeria species. Coccidia infections cause, as a rule, weight depression and bloody fecal excretions which occur as a result of lesions in the intestinal mucosa. In the case of poultry, severe coccidia infections lead, as a rule, also to higher mortality.

The use of the combinations according to the invention result in substantial advantages compared with the corresponding individual active substances sine smaller quantities of coccidiocidal agents can be employed. This results in a reduction in the toxic side effects of the products compared with the administration of the individual active substances, an increased efficiency and also a reduction in the residues in the edible tissues of the poultry.

In the agents according to the invention, the weight ratios of the active substances may vary in wide limits in order to achieve synergistic results. In the case of combinations of maduramicin (a) with meticlorpindol they are preferably between 1:3 to 1:100, in particular between 1:8 to 1:63,
(b) with methyl benzoquate they are preferably between 5:1 to 1:20, in particular between 4:1 to 1:2.5,
(c) with halofuginone they are preferably between 10:1 to 1:2, in particular between 5.3:1 to 1:1,
(d) with a mixture of meticlorpindol and methyl benzoquate they are preferably between 1:1 to 1:80, in particular 1:2 to 1:15,
(e) with amprolium there are preferably between 1:20 and 1:100,
(f) with beclotiamine they are preferably between 1:8 and 1:83,
(g) with a mixture of amprolium and ethopabate they are preferably between 1:6 and 1:67, (in each case the ratio of maduramicin to the combination partner is given).

The ratio of meticlorpindol to methyl benzoquate in case (d) may vary preferably between 20:1 to 7:1, while the ratio of amprolium to ethopabate in case (g) varies preferably between 30:1 and 10:1.

The combinations according to the invention are quite generally suitable for protecting poultry, i.e. for treating useful farm poultry, such as chickens, turkeys, ducks or geese or also other birds, such as, for example, pheasants, quails or guinea fowl; the latter types of fowl are recently all being kept in farms for economic exploitation and, like chickens, are frequently and severely attacked by coccidia.

The agents according to the invention may be employed at any time for successfully protecting poultry against coccidiosis. They may, in particular, find application in broiler farms or poultry rearing houses for pullets where a high burden of infection is produced for the poultry population because of the permanent forms of the coccidia (oocysts) which are constantly being excreted in the droppings. Since the risk of a coccidiosis outbreak always exists under these circumstances, the coccidiocidal agents according to the invention should be employed, in the case of poultry, continuously and before the outbreak of coccidiosis. The agents according to the invention may, however, also be administered during short time intervals, i.e. a few days.

The employment of the agents according to the invention and methods for combating coccidiosis are carried out in the normal manner. In accordance with the localization of the coccidia in the intestinal tract, an oral administration is primarily suitable. The active substance combinations according to the invention may in this case be mixed with feedstuffs or with drinking water.

The active substance concentrations of the combinations in feedstuffs or in drinking water may vary within certain limits. They are in general between 5 and 300 ppm of the active substance combination referred to the feedstuff or drinking water.

The particularly preferred concentrations for combating coccidiosis are, in the case of feedstuff, in each case 1.5 to 5 ppm, in particular 2 to 4 ppm, of maduramicin and (a) 15 to 150 ppm, in particular 30 to 125 ppm of meticlorpindol,
(b) 1 to 30 ppm, in particular 1.25 to 5 ppm of methyl benzoquate,
(c) 0.5 to 3 ppm, in particular 0.75 to 1.5 ppm of halofuginone and
(d) 5 to 120 ppm, in particular 8 to 30 ppm of meticlorpindol/methyl benzoquate,
(e) 100 to 150 ppm of amprolium,
(f) 40 to 125 ppm of beclotiamine,
(g) 30 to 100 ppm of amprolium/ethopabate.

In the case of use in drinking water, approximately half the specified concentrations is preferably used in each case.

All the concentrations, ratios, parts, quantities or percentages mentioned are based on weight units.

The active substance concentrations of the coccidiocidal agents are based on the feed or drinking water preparations ad lib, i.e. for free feed or drinking water consumption during a normal practical fattening or rearing period. Because of special factors due to practical conditions, it may however happen that the poultry expert has to adjust these applied concentrations upwards if the poultry have to be supplied with different feed or water stocks. In that case, however, only a portion of the feed or water stocks contain the agents according to the invention.

All the feed formulations conventional in the poultry industry are suitable as carriers for the synergistically active coccidiocidal agents according to the invention. The formulations specified below for poultry feed are examples of normal practical formulations. In addition, it is also possible, however, to use other feedstuffs based on some types of cereal grains which contain vitamin concentrates, mineral concentrates or other active substances and feed additives in any concentration. Both conventional dry mealy or pelletized feedstuffs and also liquid feed suspensions including feedstuffs such as distillers' residues and milk by-products can be used in the case of the agents according to the invention.

To prepare the poultry feed according to the invention, a concentrated premix is usually first made up which contains the synergistically active coccidiocidal agents in high concentration, for example, from 0.2 to 75%. For this purpose, the coccidiocidal agents are either dispersed or mixed in inert carrier substances, such as vermiculite, diatomaceous earth, attapulgite, calcium carbonate or Bolus alba, together with physiologically harmless carriers, such as propylene glycols, polyethylene glycols, inert oils such as vegetable oils, highly refined mineral oils, ethanol, water, or aqueous alcohols. Organic carrier materials, such as wheat bran, shredded maize, soybean flour, lucerne meal, rice husks or ground maize cobs and any other organic carrier substances from vegetable products are likewise suitable for this purpose.

The synergistically active agents according to the invention may furthermore also be administered to poultry together with the drinking water. Its inclusion in the drinking water is achieved by adding a form of the agent concerned which is soluble in water or can be suspended in water to the drinking water in a suitable quantity. Such preparations are in general produced by selecting a water-soluble form of the agent. If these are undesirable or cannot be prepared, water-insoluble forms, for example suspensions, may be used. To produce the preparations, use is made of physiologically harmless auxiliary agents which keep the coccidiocidal agents according to the invention in suspension in water over a prolonged period. Auxiliary agents which are suitable for this purpose are swelling agents, such as alginates, gelatin, carboxymethylcellulose or polyvinylpyrrolidone. The agents according to the invention may, however, be suspended also with various surfactant compounds, such as, for example, by means of lecithin, napthalenesulfonates, alkylbenzenesulfonates, alkylphenolpolyethylene oxide adducts or polyoxyethylene sorbitan esters. Normally a concentrated suspension or even a dry formulation of the coccidiocidal agent according to the invention and the suspension agents is produced in certain mixing ratios and it is then diluted with the drinking water to the required application concentration or the premixes are mixed in suitable concentrations with the feedstuffs normal in practice. The drinking water or feed so medicated is then fed to the poultry either initially ad lib or for a certain period.

The treatment method according to the invention can also be extended to other methods for treating and feeding poultry. Thus, for example, the preparations according to the invention may be combined with other active substances, such as, for example, with growth-promoting agents or antiparasitics, which are, on the one hand, synthetic agents or, on the other hand, fermentation products in the widest sense.

Although the invention is to a particular extent directed at the protection of poultry against coccidia infections, it can, however, also be applied analogously to other domestic and useful animals, such as, for example, other birds, rabbits, pigs and ruminants.

The subject of the invention is therefore also a method for treating coccidiosis in poultry, wherein the abovementioned active agents are administered orally ad lib to poultry, and in particular, either as feedstuff or by means of drinking water.

The invention is explained by the Examples below.

A.

EXAMPLES OF ANIMAL FEED COMPOSITIONS

The following examples relate to animal feed compositions which can be used for administering the active substance combination according to the invention.

| I. | Fattening feed for broilers | |
|---|---|---|
| | Composition in weight % | |
| | Fishmeal (60–65%) | 6.0 |
| | Feeding yeast | 2.0 |
| | Beef dripping | 4.7 |
| | Coarse soybean meal (44%) | 24.0 |
| | Lucerne green meal | 1.0 |
| | Maize | 44.89 |
| | Wheat | 6.35 |
| | Coarse wheat flour | 8.5 |
| | Phosphate feed lime | 1.4 |
| | Carbonate feed lime | 0.96 |
| | Trace element premix* | 0.04 |
| | Cattle salt | 0.09 |
| | Methionine DL | 0.07 |
| | | 100.0 |
| | (a) The following are added per kg of feed: | |

-continued

|  |  |  |  |
|---|---|---|---|
| Vitamin A | I.U. | 12,000 |  |
| D₃ | I.U. | 1,500 |  |
| E | mg | 18 |  |
| B₁ | mg | 1.5 |  |
| B₂ | mg | 6 |  |
| Pantothenic acid | mg | 9 |  |
| Nicotinic acid | mg | 24 |  |
| Vitamin B₆ | mg | 4.5 |  |
| B₁₂ | μg | 24 |  |
| K₃ | mg | 3 |  |
| Choline chloride | mg | 1,300 |  |
| *(b) 1.0 kg of feed contain |  |  |  |
| Mn | mg | 106 |  |
| Zn | mg | 71 |  |
| Fe | mg | 44 |  |
| Cu | mg | 3.56 |  |
| I | mg | 0.4 |  |
| Co | mg | 0.16 |  |

II. Rearing feed for chickens (0–8 weeks)

Composition in % by weight

| Fishmeal (60–65%) | 5.0 |
|---|---|
| Lucerne green meal | 6.0 |
| Coarse soybean meal (44%) | 13.0 |
| Feeding yeast | 2.8 |
| Beef dripping | 2.0 |
| Barley | 6.0 |
| Oats | 6.0 |
| Maize | 37.0 |
| Wheat | 13.0 |
| Wheat bran | 7.3 |
| Carbonate feed lime | 1.29 |
| ®Hostaphos | 0.57 |
| Trace element premix* | 0.04 |
|  | 100.0 |

III. Rearing for chickens (9–20 weeks)

Composition in % by weight

| Lucerne green meal | 6.0 |
|---|---|
| Coarse soybean meal (44%) | 10.24 |
| Feeding yeast | 1.8 |
| Beef dripping | 2.0 |
| Barley | 8.0 |
| Oats | 6.0 |
| Maize | 40.0 |
| Wheat | 15.0 |
| Wheat bran | 8.3 |
| Carbonate feed lime | 1.53 |
| ®Hostaphos | 1.02 |
| Trace element premix** | 0.04 |
| Methionine DL | 0.07 |
|  | 100.0 |

IV. Rearing feed for chickens (from 21st week onwards)

Composition in % by weight

| Fishmeal (60–65%) | 1.5 |
|---|---|
| Coarse soybean meal (44%) | 19.31 |
| Beef dripping | 1.0 |
| Oats | 6.7 |
| Maize | 40.0 |
| Wheat | 18.0 |
| Coarse wheat flour | 3.0 |
| Methionine DL | 0.07 |
| Feed paprika | 0.3 |
| Carbonate feed lime | 8.16 |
| ®Hosaphos | 1.91 |
| Trace element premix*** | 0.05 |
|  | 100.0 |

V. Feed for turkeys (composition in % by weight)

|  | Turkey starter feed 0–8 week | Turkey fattening feed I 9–12 weeks | Turkey fattening feed II 13–16 weeks |
|---|---|---|---|
| Fishmeal | 9.0 | 5.0 | 2.0 |
| Feeding yeast | 4.5 | 2.91 | 4.0 |
| Fat |  | 3.1 | 6.7 |
| Coarse soybean meal | 26.0 | 23.9 | 23.87 |
| Lucerne green meal | 4.6 | 2.0 | 0.95 |
| Barley | 5.3 | 4.5 | 5.0 |
| Oats |  | 1.0 | 4.45 |
| Maize | 36.04 | 40.02 | 39.90 |
| Wheat | 5.3 | 6.0 | 5.0 |
| Coarse wheat flour | 5.95 | 4.0 | 3.8 |
| Wheat bran |  | 4.0 |  |
| Phosphate feed lime | 1.58 | 1.30 | 2.71 |
| Carbonate feed lime | 1.35 | 1.29 | 0.96 |
| Trace element premix**** | 0.04 | 0.04 | 0.04 |
| Cattle salt | 0.24 | 0.84 | 0.44 |
| Methionine | 0.1 | 0.1 | 0.18 |
|  | 100.0 | 100.0 | 100.0 |

Vitamin mixture per kg of feed:

| Vitamin A | I.U. | 12,000 | 8,000 | 8,000 |
|---|---|---|---|---|
| D₃ | I.U. | 1,500 | 1,000 | 1,000 |
| E | mg | 18 | 12 | 12 |
| B₁ | mg | 1.5 | 1 | 1 |
| B₂ | mg | 6.0 | 4 | 4 |
| Pantothenic acid | mg | 9.0 | 6 | 6 |
| Nicotinic acid | mg | 24.0 | 16 | 16 |
| Vitamin B₆ | mg | 4.5 | 3 | 3 |
| B₁₂ | μg | 24.0 | 16 | 16 |
| K₃ | mg | 3.0 | 2 | 2 |
| Choline chloride | mg | 1,300 | 1,300 | 1,300 |

*see Example I (b); furthermore, as described in Example I (a), vitamins are added.
**see Example I (b): firthermore, vitamins are added, see Example I (a).
***Furthermore vitamins are added as described in Example I (a).
****1 kg of feed contains: 106 mg of Mn; 71 mg of Zn; 44 mg of Fe; 3.56 mg of Cu; 0.4 mg of 0.16 mg of Co.

B.

BIOLOGICAL EXAMPLES

The coccidiostatic effect of the present agents was investigated on chickens infected with coccidia. The experimental investigations cited below show the effectiveness of the various combinations according to the invention on the basis of some examples. the maduramicin is in this case employed in the form of the ammonium salt as a 1% formulation ($^R$Cygro, a commercial product manufactured by American Cyanamid).

To determine and assess the coccidiostatic effect of the agents to the invention, in all the experimental investigations described below, so-called infection controls (untreated, infected animals) and O controls (untreated, uninfected animals) were used. The animals used for this purpose of both sexes (LSL chickens supplied by Lohmann, Wallau, FRG) were randomized and in each case made up into groups of 16 animals. The infected groups treated with the agents according to the invention were made up by the same method. The animals, except those of the O control were infected with a virulent *Eimeria tenella* strain which in 8 day old chickens results in severe (reproducible) lesions of the ceca. The coccidiocidal agents were mixed with the feed for the poultry in ppm quantities; the concentrations in each case are evident from the following Tables 1a to 1f.

The degree of the pathological and anatomical changes of the intestinal mucosa in the ceca due to the infection is normally expressed (Experimental Parasitology, Vol. 28, 1970; or Long, P. L.: The Biology of the Coccidia, 1982, Univ. Park Press) in the form of damage figures (=lesion figures), hereinafter termed "lesion scores" (scale from 0 to 4). At the end of the investigations, the animals were killed 5 days after the infection and they were all investigated for typical pathological anatomical changes produced by coccidiosis.

Description and assessment of the damage (lesion scores): 0 to 4

0 = animals in which no lesions can be detected in the intestinal tract,
1 = animals with few, circumscribed small lesions (petechiae) in the ceca,
2 = animals with several, circumscribed and somewhat larger lesions (petechiae) than described under 1,
3 = animals with numerous and relatively large-area, bloody lesions which in some cases run together,
4 = animals with large-area, bloody lesions which affect the entire intestinal mucosa of the ceca and also adjacent sections of the intestine (ileum or rectum). The picture which presents itself is one of a large-area hemorrhagic enteritis of the severest degree which as a rule results in the death of the animal.

For the lesion scores specified under 1 to 4, fluid and bloody droppings are deposited to an increasing extent. The weight depression as a result of the refusal of nutrient corresponds likewise to the increase in the lesion scores.

From the observations mentioned, the relevance of the lesion scores for assessing the coccidiocidal action of the agents according to the invention becomes clear.

The lesion scores are listed on the one hand as individual values for each animal within a group and on the other hand as average values for the corresponding group of animals in the Tables 1a-1f.

TREATMENT AND INFECTIONS

In all the experiments, in each case 16 one week old LSL chickens per group were kept under constant room conditions in wire cages with 4 animals in each wire cage.

The feed medicated with the agents according to the invention was fed from day D—1 (one day before the infection) up to day D—5 (5 days after the infection) ad lib. The control groups (0 group or infection control) did not receive medicated feed. The respective groups of animals were consequently fed for 7 days with the same feed. On the day of the infection (=D0) each animal was administered 200,000 sporulated oocysts of the abovementioned E. tenella strain using a stomach tube.

After digestion of the oocysts in the small intestine, these permanent forms released the infectious sporozoites which then attack the epithelial cells of the intestinal mucosa and multiply there on a large scale by change in form. The numerous schizonts which develop from the sporozoites destroy the intestinal epithelium as a result of repeated division processes. The maximum in the destructive effect of the schizonts on the intestinal epithelium is reached 5 days after the infection. The lesion scores were therefore determined at this instant in time in the manner described above.

The synergistic effect of the agents according to the invention (combinations) is shown below in the Tables 1a-1f, and in particular on the one hand, the effect of the individual active substances in the normal practical application concentration and, on the other hand, the more than-additive or synergistic effect resulting from different combinations of the individual active substances. The lesion scores of the infection controls or O controls (uninfected animals) serve to balance the medicated and infected groups of animals in each case.

TABLE 1a

| Combinations of ammonium salt of maduramicin with metic lorpindol | | | | | | | | | | | | |
|---|---|---|---|---|---|---|---|---|---|---|---|---|
| Treatment medicated feed | Concentration pppm | Damage (lesion scores) Individual value per animal | | | | | | | | Total | Average value per group |
| none infection control | 0 | 3 4 | 3 4 | 3 4 | 3 4 | 3 4 | 3 4 | 3 4 | 4 4 | 57 | 3.6 |
| none uninfected control | 0 | 0 0 | 0 0 | 0 0 | 0 0 | 0 0 | 0 0 | 0 0 | 0 0 | 0 | 0 |
| Ammonium salt of maduramicin | 5 | 0 0 | 0 0 | 0 0 | 0 0 | 0 0 | 0 0 | 0 0 | 0 0 | 1 | 0.1 |
| | 2.5 | 0 3 0 | 0 3 0 | 0 3 0 | 2 3 0 | 2 3 0 | 2 4 0 | 3 4 0 | 3 4 0 | 39 | 2.4 |
| Meticlorpindol | 125 | 0 0 | 0 0 | 0 0 | 0 0 | 0 0 | 0 0 | 0 0 | 0 0 | 0 | 0 |
| | 60 | 0 0 | 0 0 | 0 0 | 0 1 | 0 1 | 0 2 | 0 3 | 0 3 | 10 | 0.6 |
| | 30 | 0 4 0 | 1 4 0 | 3 4 0 | 3 4 0 | 3 4 0 | 3 4 0 | 3 4 0 | 4 4 0 | 52 | 3.3 |
| Ammonium salt of maduramicin + meticlorpindol | 2.5 + 60 | 0 | 0 | 0 | 0 | 0 | 0 | 0 | 1 | 1 | 0.1 |
| | 2.5 + 30 | 0 0 | 0 0 | 0 0 | 0 0 | 0 1 | 0 1 | 0 1 | 0 1 | 1 | 0.3 |

TABLE 1b

| Combinations of ammonium salt of maduramicin with methyl benzoquate | | | | | | | | | | | | |
|---|---|---|---|---|---|---|---|---|---|---|---|---|
| Treatment medicated feed | Concentration ppm | Damage (lesion scores) Individual value per animal | | | | | | | | Total | Average value per group |
| none infection control | 0 | 3 4 | 3 4 | 3 4 | 3 4 | 3 4 | 3 4 | 3 4 | 4 4 | 57 | 3.6 |
| none uninfected control | 0 | 0 0 | 0 0 | 0 0 | 0 0 | 0 0 | 0 0 | 0 0 | 0 0 | 0 | 0 |
| Ammonium salt of maduramicin | 5 | 0 0 | 0 0 | 0 0 | 0 2 | 0 2 | 0 2 | 0 3 | 1 3 | 1 | 0.1 |

TABLE 1b-continued

Combinations of ammonium salt of maduramicin with methyl benzoquate

| Treatment medicated feed | Concentration ppm | Damage (lesion scores) Individual value per animal | | | | | | | | Total | Average value per group |
|---|---|---|---|---|---|---|---|---|---|---|---|
| | 2.5 | 3 | 3 | 3 | 3 | 3 | 4 | 4 | 4 | 39 | 2.4 |
| | | 0 | 1 | 1 | 3 | 3 | 3 | 4 | 4 | | |
| | 1.25 | 4 | 4 | 4 | 4 | 4 | 4 | 4 | 4 | 51 | 3.2 |
| | | 0 | 0 | 0 | 0 | 0 | 0 | 0 | 0 | | |
| | 10 | 0 | 0 | 0 | 0 | 0 | 0 | 0 | 0 | 0 | 0 |
| | | 0 | 0 | 0 | 0 | 1 | 1 | 1 | 1 | | |
| | 2.5 | 1 | 3 | 3 | 3 | 4 | 4 | 4 | 4 | 30 | 1.9 |
| | | 0 | 0 | 0 | 0 | 0 | 0 | 0 | 0 | | |
| Ammonium salt of maduramicin + methyl benzoquate | 2.5 + 2.5 | 0 | 0 | 0 | 0 | 0 | 0 | 0 | 0 | 0 | 0 |
| | | 0 | 0 | 0 | 0 | 0 | 0 | 0 | 0 | | |
| | 1.25 + 2.5 | 0 | 0 | 0 | 0 | 0 | 0 | 0 | 0 | 0 | 0 |

TABLE 1c

Combinations of ammonium salt of maduramicin with halofuginone

| Treatment medicated feed | Concentration ppm | Damage (lesion scores) Individual value per animal | | | | | | | | Total | Average value per group |
|---|---|---|---|---|---|---|---|---|---|---|---|
| none infection control | 0 | 3 | 3 | 3 | 3 | 3 | 3 | 3 | 4 | 57 | 3.6 |
| | | 4 | 4 | 4 | 4 | 4 | 4 | 4 | 4 | | |
| none uninfected control | 0 | 0 | 0 | 0 | 0 | 0 | 0 | 0 | 0 | 0 | 0 |
| | | 0 | 0 | 0 | 0 | 0 | 0 | 0 | 0 | | |
| | 5 | 0 | 0 | 0 | 0 | 0 | 0 | 1 | 1 | 2 | 0.1 |
| Ammonium salt of maduramicin | | | | | | | | | | | |
| | | 0 | 1 | 1 | 1 | 1 | 2 | 3 | 3 | | |
| | 2.5 | 3 | 3 | 3 | 3 | 3 | 4 | 4 | 4 | 39 | 2.4 |
| | | 0 | 0 | 0 | 0 | 0 | 0 | 0 | 0 | | |
| | 3 | 0 | 0 | 0 | 0 | 0 | 0 | 0 | 0 | 0 | 0 |
| Halofuginone | | 0 | 0 | 0 | 0 | 0 | 0 | 0 | 0 | | |
| | 1.5 | 0 | 1 | 1 | 1 | 1 | 3 | 3 | 3 | 13 | 0.8 |
| | | 1 | 1 | 3 | 3 | 3 | 3 | 3 | 3 | | |
| | 0.75 | 3 | 4 | 4 | 4 | 4 | 4 | 4 | 4 | 51 | 3.2 |
| | | 0 | 0 | 0 | 0 | 0 | 0 | 0 | 0 | | |
| Ammonium salt of maduramicin | 2.5 + 1.5 | 0 | 0 | 0 | 0 | 0 | 0 | 0 | 0 | 0 | 0 |
| | | 0 | 0 | 0 | 0 | 0 | 0 | 0 | 0 | | |
| | 2.5 + 0.75 | 0 | 0 | 0 | 0 | 0 | 1 | 3 | 3 | 3/7 | 0.4 |

TABLE 1d

Combinations of ammonium salt of maduramicin with metic lorpindol/methyl benzoquate

| Treatment medicatd feed | Concentration ppm | Damage (lesion scores) Individual value per animal | | | | | | | | Total | Average value per group |
|---|---|---|---|---|---|---|---|---|---|---|---|
| none infection control | 0 | 3 | 3 | 3 | 3 | 3 | 3 | 3 | 4 | 57 | 3.6 |
| | | 4 | 4 | 4 | 4 | 4 | 4 | 4 | 4 | | |
| none uninfected control | 0 | 0 | 0 | 0 | 0 | 0 | 0 | 0 | 0 | 0 | 0 |
| | | 0 | 0 | 0 | 0 | 0 | 0 | 0 | 0 | | |
| | 5 | 0 | 0 | 0 | 0 | 0 | 0 | 1 | 1 | 2 | 0.1 |
| Ammonium salt of maduramicin | | | | | | | | | | | |
| | | 0 | 1 | 1 | 1 | 1 | 2 | 3 | 3 | | |
| | 2.5 | 3 | 3 | 3 | 3 | 3 | 4 | 4 | 4 | 39 | 2.4 |
| | | 0 | 0 | 0 | 0 | 0 | 0 | 0 | 0 | | |
| | 108.35 | 0 | 0 | 0 | 0 | 0 | 0 | 0 | 0 | 0 | 0 |
| Meticlorpindol/ methyl benzoquate (100 + 9.35 parts) | | 0 | 0 | 0 | 0 | 1 | 1 | 1 | 1 | | |
| | 9.5 | 1 | 2 | 3 | 3 | 4 | 4 | 4 | 4 | 29 | 1.8 |
| | | 1 | 1 | 1 | 3 | 4 | 4 | 4 | 4 | | |
| | 6.75 | 4 | 4 | 4 | 4 | 4 | 4 | 4 | 4 | 54 | 3.4 |
| | | 0 | 0 | 0 | 0 | 0 | 0 | 0 | 0 | | |
| Ammonium salt of maduramicin methyl benzoquate | 2.5 + 9.5 | 0 | 0 | 0 | 0 | 0 | 0 | 0 | 1 | 1 | 0.1 |
| | | 0 | 0 | 0 | 0 | 0 | 0 | 0 | 0 | | |
| | 2.5 + 6.75 | 0 | 0 | 3 | 3 | 3 | 3 | 3 | 3 | 18 | 1.1 |

TABLE 1e

Combinations of ammonium salt of maduramicin with amprolium/ethopabate

| Treatment medicated feed | Concentration ppm | Damage (lesion scores) Individual value per animal | | | | | | | | Total | Average value per group |
|---|---|---|---|---|---|---|---|---|---|---|---|
| none | | 2 | 3 | 3 | 3 | 3 | 3 | 4 | 4 | | |
| infection control | 0 | 4 | 4 | 4 | 4 | 4 | 4 | 4 | 4 | 57 | 3.6 |
| | | 0 | 0 | 0 | 0 | 0 | 0 | 0 | 0 | | |
| uninfected control | 0 | 0 | 0 | 0 | 0 | 0 | 0 | 0 | 0 | 0 | 0 |
| | | 0 | 0 | 0 | 0 | 0 | 0 | 0 | 0 | | |
| | 5 | 0 | 0 | 0 | 0 | 0 | 0 | 1 | 1 | 2 | 0.1 |
| Ammonium salt of maduramicin | | | | | | | | | | | |
| | | 0 | 1 | 1 | 1 | 1 | 2 | 3 | 3 | | |
| | 2.5 | 3 | 3 | 3 | 3 | 3 | 4 | 4 | 4 | 39 | 2.4 |
| | | 0 | 0 | 0 | 0 | 0 | 0 | 0 | 0 | | |
| | 125 | 0 | 0 | 0 | 0 | 0 | 0 | 0 | 0 | 0 | 0 |
| Amprolium + ethopabate (100 + 6.4 parts) | | | | | | | | | | | |
| | | 0 | 0 | 0 | 0 | 0 | 0 | 0 | 0 | | |
| | 62.5 | 0 | 0 | 0 | 0 | 0 | 1 | 3 | 3 | 7 | 0.4 |
| | | 0 | 0 | 0 | 0 | 0 | 0 | 0 | 1 | | |
| | 31.25 | 1 | 1 | 3 | 3 | 3 | 3 | 3 | 4 | 22 | 1.4 |
| | | 0 | 0 | 0 | 0 | 0 | 0 | 0 | 0 | | |
| Ammonium salt of maduramicin + amprolium/ethopabate | 2.5 + 62.5 | 0 | 0 | 0 | 0 | 0 | 0 | 0 | 0 | 0 | 0 |
| | 2.5 + 31.25 | 0 | 0 | 0 | 0 | 0 | 0 | 0 | 0 | 0 | 0 |

TABLE 1f

Combinations of ammonium salt of maduramicin with amprolium

| Treatment medicated feed | Concentration ppm | Damage (lesion scores) Individual valuer per animal | | | | | | | | Total | Average value per group |
|---|---|---|---|---|---|---|---|---|---|---|---|
| none | | 3 | 3 | 3 | 3 | 4 | 4 | 4 | 4 | | |
| infection control | 0 | 4 | 4 | 4 | 4 | 4 | 4 | 4 | 4 | 60 | 3.8 |
| none | | 0 | 0 | 0 | 0 | 0 | 0 | 0 | 0 | | |
| uninfected control | 0 | 0 | 0 | 0 | 0 | 0 | 0 | 0 | 0 | 0 | 0 |
| | | 0 | 0 | 0 | 0 | 0 | 0 | 0 | 0 | | |
| | 5 | 0 | 0 | 0 | 0 | 0 | 1 | 1 | 2 | 4 | 0.3 |
| Ammonium salt of maduramicin | | | | | | | | | | | |
| | | 0 | 0 | 1 | 1 | 1 | 2 | 2 | 3 | | |
| | 2.5 | 3 | 3 | 3 | 4 | 4 | 4 | 4 | 4 | 39 | 2.4 |
| | | 0 | 0 | 0 | 0 | 0 | 0 | 0 | 0 | | |
| | 125 | 0 | 0 | 0 | 0 | 0 | 0 | 0 | 0 | 0 | 0 |
| Amprolium | | | | | | | | | | | |
| | | 0 | 0 | 0 | 0 | 0 | 0 | 0 | 0 | | |
| | 62.5 | 0 | 0 | 0 | 0 | 1 | 3 | 3 | 3 | 10 | 0.6 |
| | | 0 | 0 | 0 | 0 | 0 | 0 | 0 | 0 | | |
| | 31.25 | 1 | 3 | 3 | 3 | 3 | 4 | 4 | 4 | 25 | 1.6 |
| | | 0 | 0 | 0 | 0 | 0 | 0 | 0 | 0 | | |
| Ammonium salt of maduramicin + amprolium | 2.5 + 62.5 | 0 | 0 | 0 | 0 | 0 | 0 | 0 | 0 | 0 | 0 |
| | | 0 | 0 | 0 | 0 | 0 | 0 | 0 | 0 | | |
| | 2.5 + 31.25 | 0 | 0 | 0 | 0 | 0 | 0 | 0 | 1 | 1 | 0.1 |

I claim:

1. A coccidiocidal composition which contains maduramicin or its physiologically acceptable salt in combination with one of the following active ingredients or ingredient mixtures in a ratio of maduramicin to said ingredients as indicated:
  (a) with meticlorpindol in a ratio between 1:12 to 24,
  (b) with methyl benzoquate in a ratio between 1:1 to 2,
  (c) with halofuginone in a ratio between 1:3 to 6,
  (d) with a mixture of 10 parts of neticlorpindol to 1 parts of methyl benzoquate in a ratio between 1:2.7 to 3.8,
  (e) with amprolium in a ratio between 1:12.5 to 25, or
  (f) with a mixture of 20 parts of amprolium to 1 part of ethopabate in a ratio between 1:12.5 to 25.

2. The composition as claimed in claim 1, which contains maduramicin in the form of its physiologically acceptable salt.

3. The composition as claimed in claim 1, which contains maduramicin as an alkali salt, alkaline earth salt or ammonium salt.

4. The composition as claimed in claim 1, which contains maduramicin as sodium salt, potassium salt or ammonium salt.

5. The composition as claimed in claim 1, which contains maduramicin as ammonium salt.

6. The composition as claimed in claim 1, which contains maduramicin in combination with meticlorpindol and methyl benzoquate.

7. The composition as claimed in claim 1, which contains maduramicin in combination with amprolium and ethopabate.

8. The composition as claimed in claim 1, which contains additionally poultry feed or drinking water.

9. The composition as claimed in claim 8, wherein the concentration of the combination of maduramicin and the other ingredients in feedstuff or in drinking water is between 5 and 300 ppm.

10. The composition as claimed in claim 1 comprising feedstuff, 1.5 to 5 ppm of maduramicin and
  (a) 15 to 150 ppm of meticlorpindol,
  (b) 1 to 30 ppm of methyl benzoquate,
  (c) 0.5 to 3 ppm of halofuginone, (d) 5 to 120 ppm of meticlorpindol and methyl benzoquate,
(e) 100 to 150 ppm of amprolium, or
(f) 30 to 100 ppm amprolium and ethopabate.

11. The composition as claimed in claim 10 comprising feedstuff, 2 to 4 ppm of maduramicin,
(a) 30 to 125 ppm of meticlorpindol,
(b) 1.25 to 5 ppm of methyl benzoquate,
(c) 0.75 to 1.5 ppm of halofuginone,
(d) 8 to 30 ppm of meticlorpindol and methyl benzoquate.

12. A method for combating coccidiosis in poultry wherein a therapeutically effective quantity of a composition sufficient to combat coccidiosis as claimed in claim 1 is orally administered to poultry.

* * * * *

UNITED STATES PATENT AND TRADEMARK OFFICE
CERTIFICATE OF CORRECTION

PATENT NO. : 4,861,758
DATED : August 29, 1989
INVENTOR(S) : Wolfgang Raether

It is certified that error appears in the above-identified patent and that said Letters Patent is hereby corrected as shown below:

Claim 1, column 11, line 56, change "1.3 to 6" to --1:.3 to .6--.

Claim 1, column 11, line 57, change "neticlorpindol" to --meticlorpindol--.

Claim 1, column 11, line 58, change "parts" to --part--.

Signed and Sealed this

Fourteenth Day of May, 1991

Attest:

HARRY F. MANBECK, JR.

Attesting Officer

Commissioner of Patents and Trademarks